US012588865B2

(12) United States Patent
Lee

(10) Patent No.: US 12,588,865 B2
(45) Date of Patent: Mar. 31, 2026

(54) ELECTRONIC DEVICE PROVIDING EXERCISE GUIDE BASED ON EXERCISE CAPACITY AND CONTROL METHOD THEREOF

(71) Applicant: SAMSUNG ELECTRONICS CO., LTD., Suwon-si (KR)

(72) Inventor: Hongji Lee, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 358 days.

(21) Appl. No.: 18/173,807

(22) Filed: Feb. 24, 2023

(65) Prior Publication Data

US 2023/0263464 A1 Aug. 24, 2023

Related U.S. Application Data

(63) Continuation of application No. PCT/KR2023/002543, filed on Feb. 22, 2023.

(30) Foreign Application Priority Data

Feb. 24, 2022 (KR) ........................ 10-2022-0024342
Mar. 24, 2022 (KR) ........................ 10-2022-0036880

(51) Int. Cl.
*A61B 5/00* (2006.01)
*A61B 5/01* (2006.01)

(52) U.S. Cl.
CPC .............. *A61B 5/4809* (2013.01); *A61B 5/01* (2013.01); *A61B 5/681* (2013.01); *A61B 5/7275* (2013.01)

(58) Field of Classification Search
CPC . A61B 2503/10; A61B 5/1118; A61B 5/4809; A61B 5/48; A61B 5/165;
(Continued)

(56) References Cited

U.S. PATENT DOCUMENTS

2009/0105560 A1 4/2009 Solomon
2011/0176578 A1 7/2011 Zei et al.
(Continued)

FOREIGN PATENT DOCUMENTS

CN 108936985 A 12/2018
CN 109637625 A 4/2019
(Continued)

OTHER PUBLICATIONS

International Search Report mailed May 30, 2023 for PCT/KR2023/002543, citing the above reference(s).
(Continued)

*Primary Examiner* — Sana Sahand
(74) *Attorney, Agent, or Firm* — CANTOR COLBURN LLP

(57) ABSTRACT

An electronic device includes a sensor module, a display, and at least one processor configured to determine whether a user is in a sleep state using the sensor module, repeatedly sense the user's skin temperature using the sensor module, based on determining that the user is in the sleep state, determine whether the user is in a non-sleep state using the sensor module while repeatedly sensing the user's skin temperature, sense the user's skin temperature using the sensor module, based on determining that the user is in the non-sleep state, determine the user's exercise capacity using the user's first temperature and second temperature determined based on the skin temperature sensed in each of the sleep state and the non-sleep state, and provide an exercise guide through the display, based on the determined exercise capacity. Further, a method for controlling the same are disclosed.

13 Claims, 10 Drawing Sheets

(58) Field of Classification Search
CPC ......... A61B 5/01; A61B 5/681; A61B 5/7275;
A61B 5/00
See application file for complete search history.

(56) References Cited

U.S. PATENT DOCUMENTS

| | | | |
|---|---|---|---|
| 2015/0251074 A1 | 9/2015 | Ahmed et al. | |
| 2016/0120048 A1 | 4/2016 | Seo et al. | |
| 2017/0331505 A1 | 11/2017 | Shim et al. | |
| 2019/0269337 A1 | 9/2019 | Ma et al. | |
| 2020/0194106 A1 | 6/2020 | Olson et al. | |
| 2021/0345878 A1 | 11/2021 | Khalil et al. | |
| 2021/0354001 A1* | 11/2021 | Kinnunen | G16H 50/70 |

FOREIGN PATENT DOCUMENTS

| | | |
|---|---|---|
| JP | 2010063766 A | 3/2010 |
| JP | 2019032641 A | 2/2019 |
| KR | 20160049858 A | 5/2016 |
| KR | 20170008550 A | 1/2017 |
| KR | 20170127744 A | 11/2017 |
| KR | 20190045475 A | 5/2019 |
| KR | 20190106092 A | 9/2019 |
| KR | 20210144087 A | 11/2021 |

OTHER PUBLICATIONS

Braid A. Macrae, "Skin Temperature Measurement Using Contact Thermometry; A Systematic Review of Setup Variables and Their Effects on Measured Values," Frontiers in Physiology, Jan. 30, 2018, vol. 9, 24 pages, XP093246145.

P. Korman et al., "Changes in body surface temperature during speed endurance work-out in highly-trained male sprinters," Infrared Physics & Technology, Aug. 2016, pp. 209-213, vol. 78, XP029757115.

The extended European search report for EP Application No. 23760379.0 mailed on Feb. 13, 2025, citing the above reference(s).

European Office Action for EP Application No. 23760379.0 mailed on Jan. 22, 2026, citing the above reference(s).

* cited by examiner

ELECTRONIC DEVICE PROVIDING EXERCISE GUIDE BASED ON EXERCISE CAPACITY AND CONTROL METHOD THEREOF

CROSS-REFERENCE TO RELATED APPLICATIONS

This application is a continuation of International Application No. PCT/KR2023/002543 designating the United States, filed on Feb. 22, 2023 in the Korean Intellectual Property Receiving Office and claiming priority to Korean Patent Application No. 10-2022-0024342, filed on Feb. 24, 2022, in the Korean Intellectual Property Office, and Korean Patent Application No. 10-2022-0036880, filed on Mar. 24, 2022, in the Korean Intellectual Property Office, the disclosures of all of which are incorporated by reference herein in their entireties.

BACKGROUND

1. Field

The disclosure relates to an electronic device that provides an exercise guide based on exercise capacity, and a method for controlling the same.

2. Description of Related Art

More and more services and additional functions are being provided through electronic devices, e.g., smartphones, or other portable electronic devices. To meet the needs of various users and raise use efficiency of electronic devices, communication service carriers or device manufacturers are jumping into competitions to develop electronic devices with differentiated and diversified functionalities. Accordingly, various functions that are provided through electronic devices are evolving more and more.

SUMMARY

Technical Problem

A conventional electronic device (e.g., smart watch) provides only a service of providing an exercise guide based on heart rate information about the user during exercise. Further, the conventional electronic device fails to provide a function or operation for continuously monitoring the user's body temperature. During exercise, since heart stress due to the heat generated inside the body increases according to exercise, if body temperature (e.g., skin temperature) may be continuously monitored, the exercise guide may be subdivided and provided according to the user's current condition.

Technical Solution

According to an embodiment of the disclosure, there may be provided an electronic device that determines the user's exercise capacity by continuously (e.g., repeatedly) monitoring the user's body temperature through the electronic device during the user's daily life and provides an exercise guide based on the determined exercise capacity.

According to an embodiment of the disclosure, there may be provided a method for controlling an electronic device that determines the user's exercise capacity by continuously (e.g., repeatedly) monitoring the user's body temperature through the electronic device during the user's daily life and provides an exercise guide based on the determined exercise capacity.

According to an embodiment of the disclosure, an electronic device includes a sensor module, a display, and at least one processor configured to determine whether a user of the electronic device is in a sleep state using the sensor module, repeatedly sense the user's skin temperature using the sensor module, based on determining that the user is in the sleep state, determine whether the user is in a non-sleep state using the sensor module while repeatedly sensing the user's skin temperature, sense the user's skin temperature using the sensor module, based on determining that the user is in the non-sleep state, determine the user's exercise capacity using the user's first temperature and second temperature determined based on the skin temperature sensed in the sleep state and the skin temperature sensed in the non-sleep state, respectively, and provide an exercise guide through the display, based on the determined exercise capacity.

According to an embodiment of the disclosure, an electronic device includes: a sensor module, a display, and at least one processor configured to determine whether a user of the electronic device is doing exercise based on data sensed by the sensor module, repeatedly sense a skin temperature of the user using the sensor module during the exercise, repeatedly identify the user's current body temperature based on the sensed skin temperature, determine an exercise capacity of the user using the identified body temperature, and provide an exercise guide through the display based on the determined exercise capacity.

According to an embodiment of the disclosure, a method for controlling an electronic device includes: determining whether a user is in a sleep state using a sensor module of the electronic device, repeatedly sensing the user's skin temperature using the sensor module, based on determining that the user is in the sleep state, determining whether the user is in a non-sleep state using the sensor module while repeatedly sensing the user's skin temperature, sensing the user's skin temperature using the sensor module, based on determining that the user is in the non-sleep state, determining the user's exercise capacity using the user's first temperature and second temperature determined based on the skin temperature sensed in the sleep state and the skin temperature sensed in the non-sleep state, respectively, and providing an exercise guide through a display of the electronic device, based on the determined exercise capacity.

The disclosure is not limited to the foregoing embodiments but various modifications or changes may rather be made thereto without departing from the spirit and scope of the disclosure.

Advantageous Effects

According to an embodiment of the disclosure, there may be provided an electronic device that determines the user's exercise capacity by continuously (e.g., repeatedly) monitoring the user's body temperature through the electronic device during the user's daily life and provides an exercise guide based on the determined exercise capacity.

The effects set forth herein are not limited thereto, and it is apparent to one of ordinary skill in the art that various effects may be disclosed herein.

DETAILED DESCRIPTION

Figure 1A:
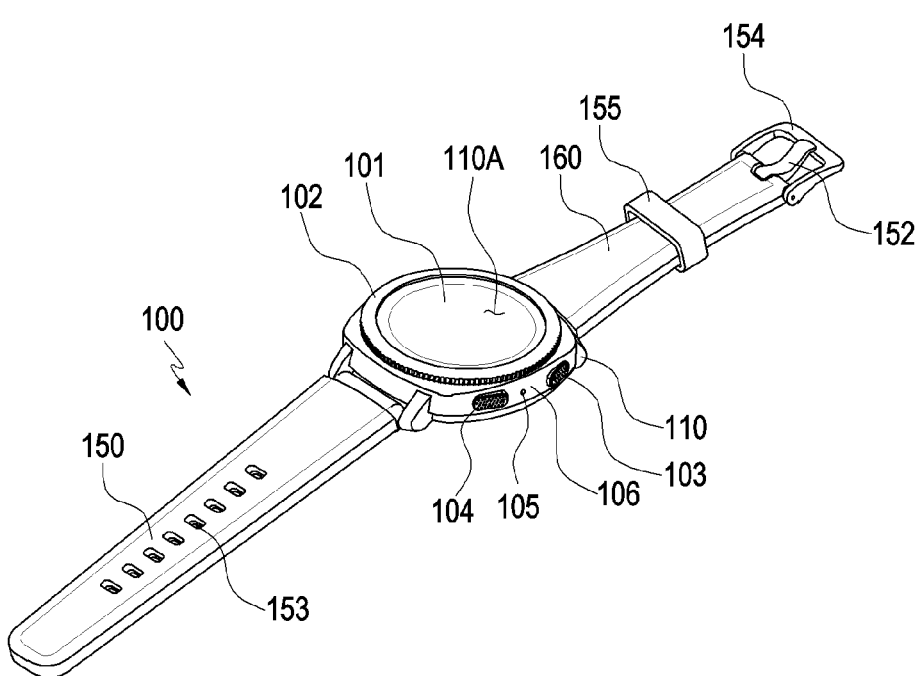
FIG. 1A is a front perspective view illustrating a mobile electronic device according to an embodiment.
Figure 1B:
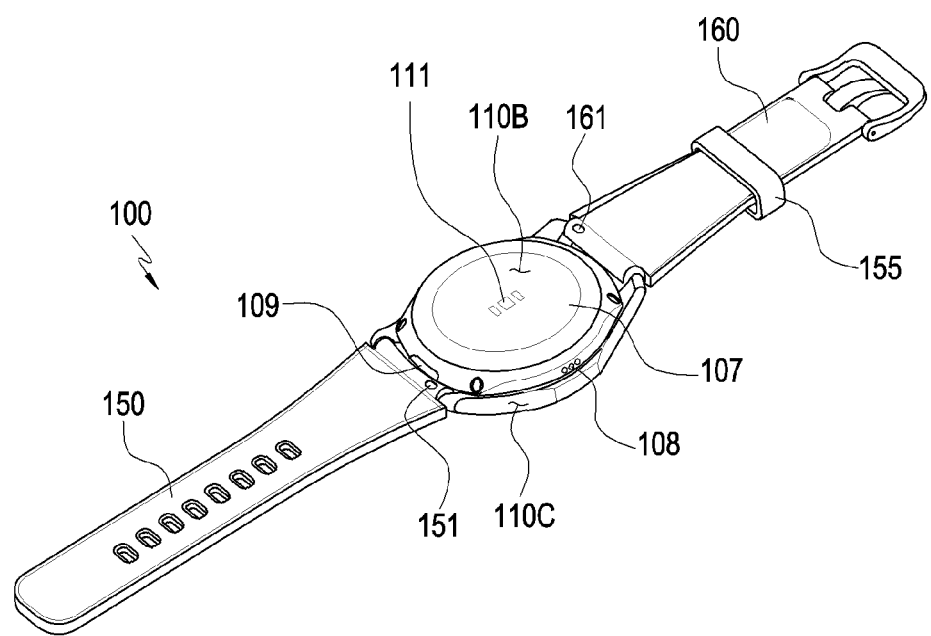
FIG. 1B is a rear perspective view illustrating an electronic device as shown in FIG. 1A.
Figure 1C:
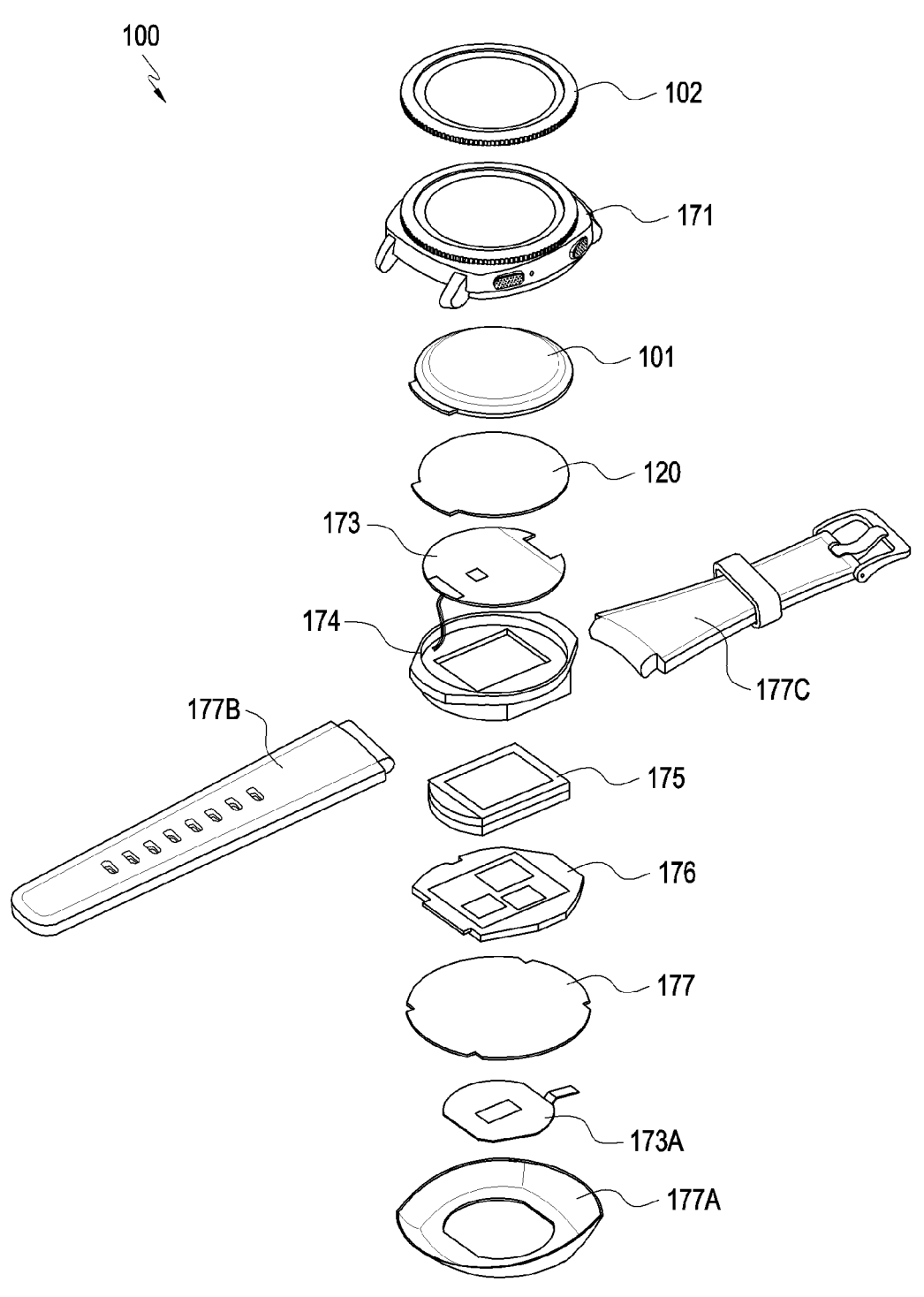
FIG. 1C is an exploded perspective view illustrating the electronic device of FIG. 1A.

FIG. 1A is a front perspective view illustrating a mobile electronic device according to an embodiment. FIG. 1B is a rear perspective view illustrating an electronic device as shown in FIG. 1A. FIG. 1C is an exploded perspective view illustrating the electronic device of FIG. 1A.

Referring to FIGS. 1A and 1B, according to an embodiment, an electronic device 100 may include a housing 110 including a first surface (or front surface) 110A, a second surface (or rear surface) 110B, and a side surface 110C surrounding the space between the first surface 110A and the second surface 110B and fastening members 150 and 160 connected to at least part of the housing 110 and configured to allow the electronic device 100 to be removably fastened on the user's body portion (e.g., the user's wrist or ankle). According to another embodiment (not shown), the housing may denote a structure forming part of the first surface 110A, the second surface 110B, and the side surface 110C of FIG. 1A. According to an embodiment, at least part of the first surface 110A may have a substantially transparent front plate 101 (e.g., a glass plate or polymer plate including various coat layers). The second surface 110B may be formed by a rear plate 107 that is substantially opaque. The rear plate 107 may be formed of, e.g., laminated or colored glass, ceramic, polymer, metal (e.g., aluminum, stainless steel (STS), or magnesium), or a combination of at least two thereof. The side surface 110C may be formed by a side bezel structure (or a "side member") 106 that couples to the front plate 101 and the rear plate 107 and includes a metal and/or polymer. According to an embodiment, the rear plate 107 and the side bezel plate 106 may be integrally formed together and include the same material (e.g., a metal, such as aluminum). The fastening members 150 and 160 may be formed of various materials in various shapes. A uni-body structure or multiple unit links which is flexible may be formed of fabric, leather, rubber, urethane, metal, ceramic, or a combination of at least two thereof.

According to an embodiment, the electronic device 100 may include at least one or more of a display 120 (refer to FIG. 1C), audio modules 105 and 108, a sensor module 111, key input devices 102, 103, and 104, and a connector hole 109. According to an embodiment, the electronic device 100 may exclude at least one (e.g., the key input devices 102, 103, and 104, connector hole 109, or sensor module 111) of the components or may add other components.

The display 120 may be exposed through a significant portion of the front plate 101. The display 120 may have a shape corresponding to the shape of the front plate 101, e.g., a circle, ellipse, or polygon. The display 120 may be coupled with, or disposed adjacent, a touch detection circuit, a pressure sensor capable of measuring the strength (pressure) of touches, and/or fingerprint sensor.

The audio modules 105 and 108 may include a microphone hole 105 and a speaker hole 108. The microphone hole 105 may have a microphone inside to obtain external sounds. According to an embodiment, there may be a plurality of microphones to be able to detect the direction of a sound. The speaker hole 108 may be used for an external speaker or a receiver for phone talks. According to an embodiment, the speaker hole 108 and the microphone hole 105 may be implemented as a single hole, or speakers may be rested without the speaker holes (e.g., piezo speakers).

The sensor module 111 may produce an electrical signal or data value corresponding to the internal operation state or external environment state of the electronic device 100. The sensor module 111 may include, e.g., a biometric sensor module 111 (e.g., a heartrate monitor (HRM) sensor) disposed on the second surface 110B of the housing 110. The electronic device 100 may include a sensor module not shown, e.g., at least one of a gesture sensor, a gyro sensor, a barometric sensor, a magnetic sensor, an acceleration sensor, a grip sensor, a color sensor, an infrared (IR) sensor, a biometric sensor, a temperature sensor, a humidity sensor, or an illuminance sensor.

The key input devices 102, 103, and 104 may include a wheel key 102 disposed on the first surface 110A of the housing 110 to be rotatable in at least one direction and/or key buttons 103 and 104 disposed on the side surface 110C of the housing 110. The wheel key 102 may have a shape corresponding to the outer shape of the front plate 101. According to another embodiment, the electronic device 100 may exclude all or some of the above-mentioned key input devices 102, 103, and 104, and the excluded key input devices 102, 103, and 104 may be implemented in other forms, e.g., as soft keys on the display 120. The connector hole 109 may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 100 may further include a connector cover (not shown) to cover at least part of, e.g., the connector hole 109 and preventing undesirable materials from entering the connector hole.

The fastening members 150 and 160 may detachably be fastened to at least portions of the housing 110 via locking members 151 and 161. The fastening members 150 and 160 may include one or more of a fixing member 152, fixing member coupling holes 153, a band guide member 154, and a band fixing ring 155.

The fixing member 152 may be configured to allow the housing 110 and the fastening members 150 and 160 to be fastened to the user's body portion (e.g., wrist or ankle). The fixing member coupling holes 153 may fasten the housing 110 and the fastening members 150 and 160 to the user's body portion, corresponding to the fixing member 152. The band guide member 154 may be configured to restrict movement of the fixing member 152 to a certain range when the fixing member 152 fits into one of the fixing member coupling holes 153, thereby allowing the fastening members 150 and 160 to be tightly fastened onto the user's body portion. The band fixing ring 155 may limit the range of movement of the fastening members 150 and 160, with the fixing member 152 fitted into one of the fixing member coupling holes 153.

Referring to FIG. 1C, the electronic device 100 may include a side bezel structure 171, a wheel key 102, a front plate 101, a display 120, a first antenna 173, a second antenna 173a, a supporting member 174 (e.g., a bracket), a battery 175, a printed circuit board 176, a sealing member 177, a rear plate 177a, and fastening members 177b and 177c. The supporting member 174 may be disposed inside the electronic device 100 to be connected with the side bezel structure 171 or integrated with the side bezel structure 171. The supporting member 174 may be formed of, e.g., a metal and/or non-metallic material (e.g., polymer). The display 120 may be joined onto one surface of the supporting member 174, and the printed circuit board 176 may be joined onto the opposite surface of the supporting member 174. A processor, memory, and/or interface may be mounted on the printed circuit board 176. The processor may include one or more of, e.g., a central processing unit, an application processor, a graphic processing unit (GPU), a sensor processor, or a communication processor.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect, e.g., the electronic device 100 with an external electronic device and may include a USB connector, an SD card/multimedia card (MMC) connector, or an audio connector.

The battery 175 may be a device for supplying power to at least one component of the electronic device 100. The battery 175 may include, e.g., a primary cell which is not rechargeable, a secondary cell which is rechargeable, or a fuel cell. At least a portion of the battery 175 may be disposed on substantially the same plane as the printed circuit board 176. The battery 175 may be integrally or detachably disposed inside the electronic device 100.

The first antenna 173 may be disposed between the display 120 and the supporting member 174. The first antenna 173 may include, e.g., a near-field communication (NFC) antenna, a wireless charging antenna, and/or a magnetic secure transmission (MST) antenna. The first antenna 173 may perform short-range communication with an external device, wirelessly transmit/receive power necessary for charging, or transmit magnetic-based signals including payment data or short-range communication signals. According to an embodiment, an antenna structure may be formed by a portion or combination of the side bezel structure 171 and/or the supporting member 174.

The second antenna 173a may be disposed between the printed circuit board 176 and the rear plate 177a. The second antenna 173a may include, e.g., a near-field communication (NFC) antenna, a wireless charging antenna, and/or a magnetic secure transmission (MST) antenna. The second antenna 173a may perform short-range communication with an external device, wirelessly transmit/receive power necessary for charging, or transmit magnetic-based signals including payment data or short-range communication signals. According to another embodiment, an antenna structure may be formed of a portion or combination of the side bezel structure 171 and/or the rear plate 177a.

The sealing member 177 may be positioned between the side bezel structure 171 and the rear plate 177a. The sealing member 177 may be configured to block moisture or foreign bodies that may enter the space surrounded by the side bezel structure 171 and the rear plate 177a, from the outside.

Figure 2:
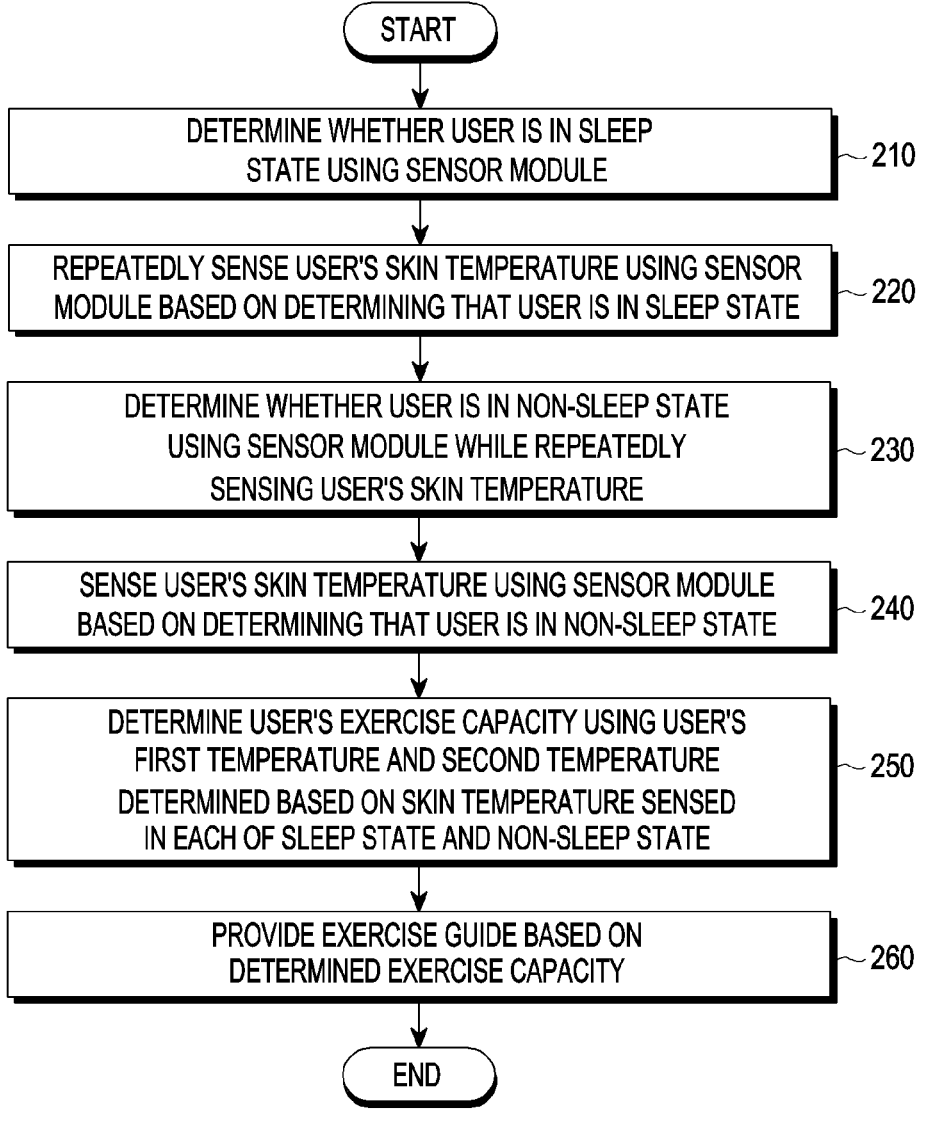
FIG. 2 is a flow chart illustrating a function or operation of determining a user's exercise capacity based on the user's body temperature sensed during the user's sleep and non-sleep (e.g., immediately after waking up) and providing an exercise guide based on the determined exercise capacity, by an electronic device, according to an embodiment of the disclosure.
Figure 3A:
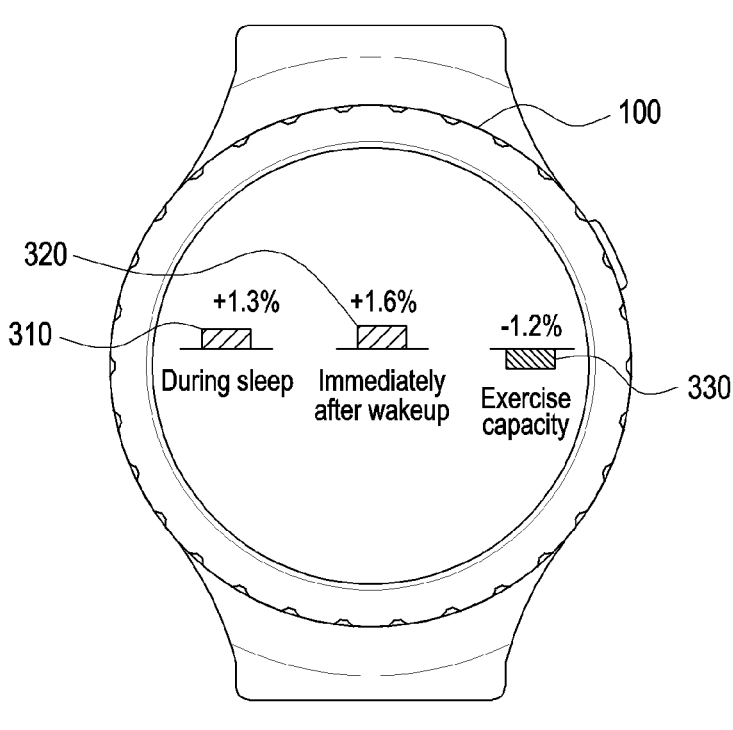
FIG. 3A is an example view illustrating a function or operation of providing information about a change rate of a body temperature and information about a change rate of exercise capacity by an electronic device according to an embodiment of the disclosure.
Figure 3B:
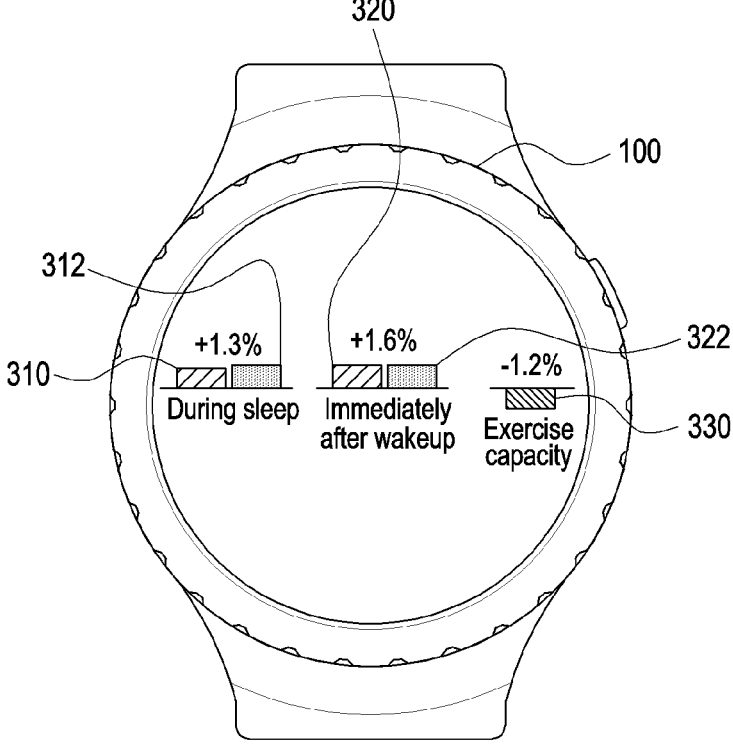
FIG. 3B is an example view illustrating a function or operation of providing information about a change rate of a skin temperature and a body temperature and information about a change rate of exercise capacity by an electronic device according to an embodiment of the disclosure.
Figure 3C:
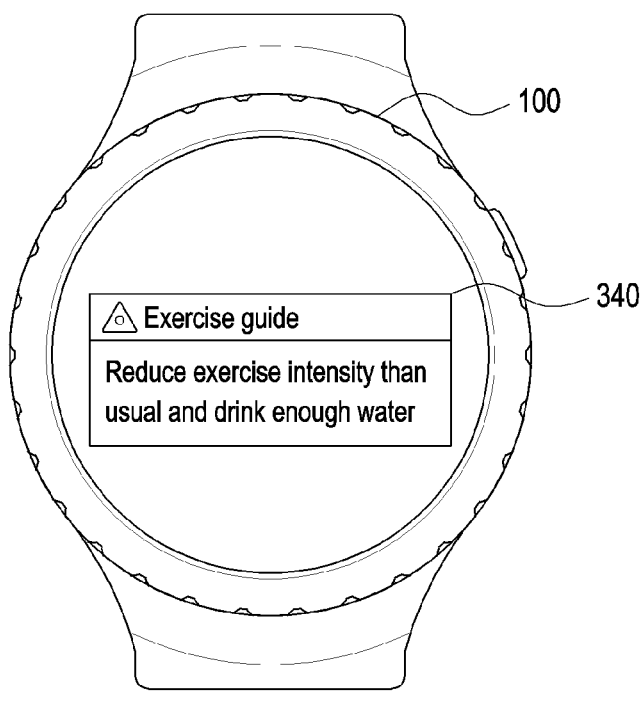
FIG. 3C is an example view illustrating a function or operation of providing an exercise guide determined based on information about a change rate of a body temperature and information about a change rate of exercise capacity by an electronic device according to an embodiment of the disclosure.
Figure 3D:
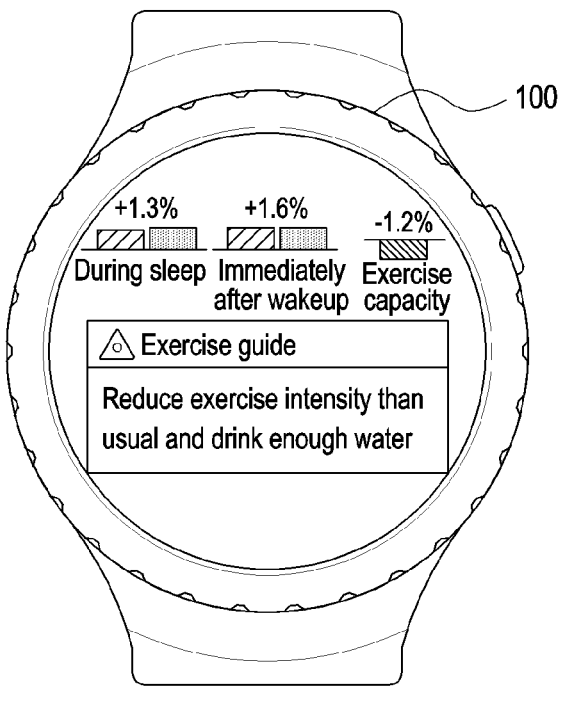
FIG. 3D is an example view illustrating a function or operation of providing, along with an exercise guide, information about a change rate of a body temperature and information about a change rate of exercise capacity by an electronic device according to an embodiment of the disclosure.

FIG. 2 is a flow chart illustrating a function or operation of determining a user's exercise capacity based on the user's body temperature sensed during the user's sleep and non-sleep (e.g., immediately after waking up) and providing an exercise guide based on the determined exercise capacity, by an electronic device 100 (e.g., the electronic device 801 of FIG. 8), according to an embodiment of the disclosure. FIG. 3A is an example view illustrating a function or operation of providing information about a change rate of a body temperature and information about a change rate of exercise capacity by an electronic device according to an embodiment of the disclosure. FIG. 3B is an example view illustrating a function or operation of providing information about a change rate of a skin temperature and a body temperature and information about a change rate of exercise capacity by an electronic device according to an embodiment of the disclosure. FIG. 3C is an example view illustrating a function or operation of providing an exercise guide determined based on information about a change rate of a body temperature and information about a change rate of exercise capacity by an electronic device according to an embodiment of the disclosure. FIG. 3D is an example view illustrating a function or operation of providing, along with an exercise guide, information about a change rate of a body temperature and information about a change rate of exercise capacity by an electronic device according to an embodiment of the disclosure.

Figure 8:
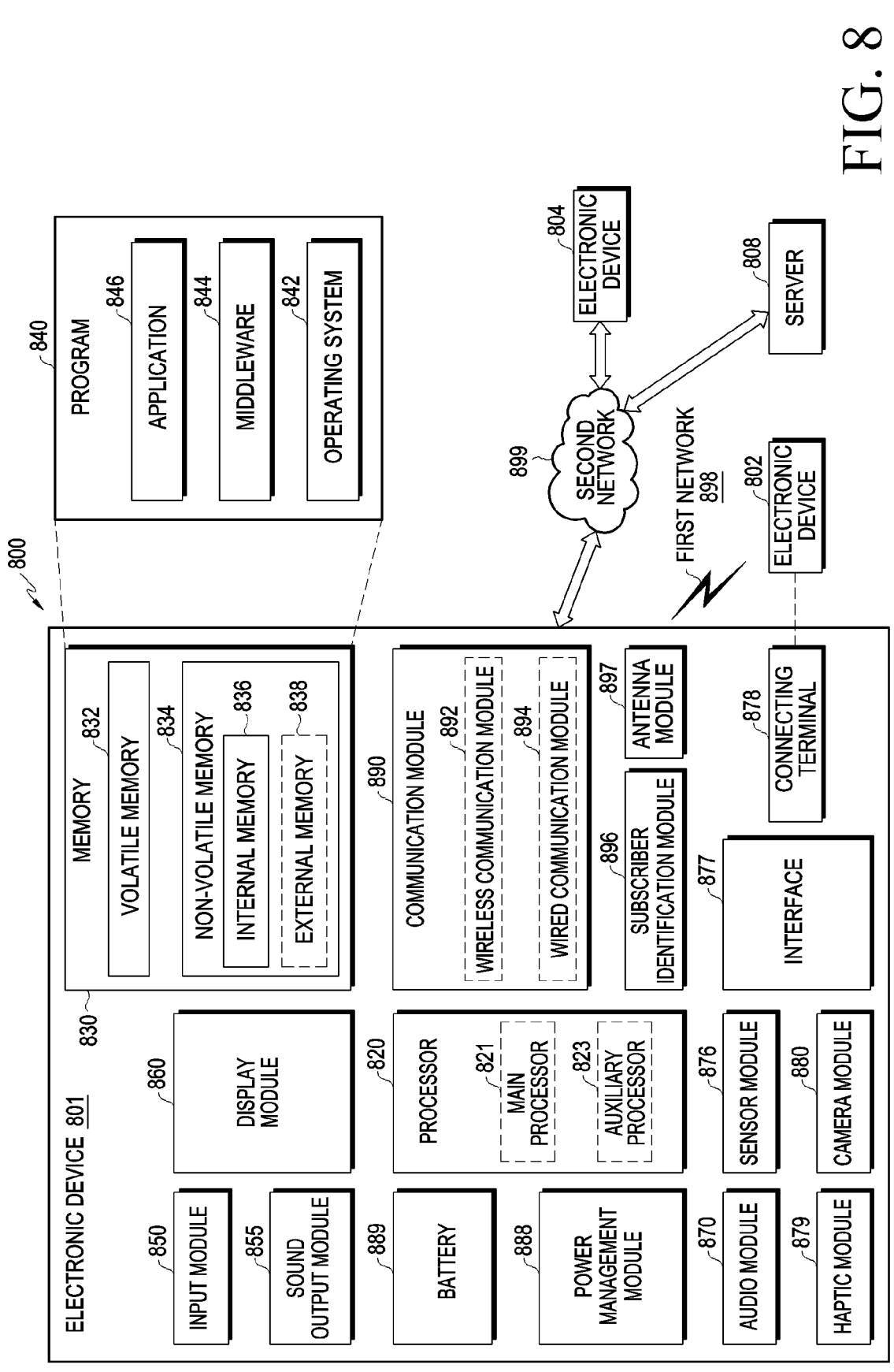
FIG. 8 is a block diagram illustrating an electronic device in a network environment according to various embodiments of the disclosure.

According to an embodiment, operations 210 to 260 may be understood as performed by a processor (e.g., the processor 820 of FIG. 8) of an electronic device (e.g., the electronic device 801 of FIG. 8).

Referring to FIG. 2, according to an embodiment of the disclosure, an electronic device 100 (e.g., the processor 820 of FIG. 8) may determine whether the user is in a sleep state using a sensor module 876 (e.g., the sensor module 876 of FIG. 8) in operation 210. According to an embodiment of the disclosure, the electronic device 100 may determine that the user is in the sleep state when the magnitude (e.g., acceleration value) of the user's motion sensed by the sensor module 876 (e.g., an accelerometer) is a preset value or less during a designated time. According to an embodiment of the disclosure, the electronic device 100 may determine that the user is in the sleep state according to the user's selection input to a physical key (e.g., a jog button or tactile key button) provided in the electronic device 100 or a specific visual object (e.g., a button indicating whether the sleep state is entered) provided through the electronic device 100. According to another embodiment of the disclosure, the electronic device 100 may determine that the user is in the sleep state when the user's selection input is not made during a designated time. According to an embodiment of the disclosure, the electronic device 100 may determine that the user is in the sleep state if a time (e.g., 12:00 AM) preset by the user is reached. According to an embodiment of the disclosure, the electronic device 100 may determine whether the user is in the sleep state using data sensed by the sensor module 876 (e.g., a photoplethysmogram (PPG) sensor). For example, according to an embodiment of the disclosure, the electronic device 100 may determine that the user is in the sleep state when biometric information (e.g., blood pressure, heartrate, blood volume, pulse rate, or respiration rate) obtained based on sensing data (e.g., blood volume in blood vessel or change in blood volume in blood vessel) sensed by the sensor module 876 (e.g., a PPG sensor) is a predesignated value or less. Other various techniques for determining whether the user is in the sleep state may be applied to operation 210.

According to an embodiment of the disclosure, in operation 220, the electronic device 100 may repeatedly (e.g., every 10 minutes) sense the user's skin temperature using the sensor module 876 (e.g., a temperature sensor) based on determining that the user is in the sleep state.

According to an embodiment of the disclosure, in operation 230, the electronic device 100 may determine whether the user is in the non-sleep state using the sensor module 876 while repeatedly sensing the user's skin temperature. According to an embodiment of the disclosure, the electronic device 100 may determine whether the user is in a wake-up state. According to an embodiment of the disclosure, the electronic device 100 may determine that the user's state switches from the sleep state to the non-sleep state (e.g., wake-up) and the user is in the non-sleep state when the magnitude (e.g., acceleration value) of the user's motion sensed by the sensor module 876 (e.g., an accelerometer) maintains a preset value or less during a designated time or more and then exceeds the preset value. According to an embodiment of the disclosure, the electronic device 100 may determine that the user is in the non-sleep state according to the user's selection input to a physical key or a specific visual object (e.g., a button indicating whether the user wakes up) provided through the electronic device 100. According to another embodiment of the disclosure, the electronic device 100 may determine that the user is in the non-sleep state when the user's selection input is not made to the electronic device 100 during the designated time (e.g., one hour) or more and then the user's selection input is obtained. According to an embodiment of the disclosure, the electronic device 100 may determine that the user is in the non-sleep state if a time (e.g., 7:00 AM) preset by the user is reached after the user enters the sleep state. Other various techniques for determining whether the user's state switches from the sleep state to the non-sleep state may be applied to operation 230.

According to an embodiment of the disclosure, in operation 240, the electronic device 100 may sense the user's skin temperature using the sensor module 876 based on determining that the user is in the non-sleep state. According to an embodiment of the disclosure, the electronic device 100 may sense the user's skin temperature within a predesignated time (e.g., 5 minutes) after the user's state switches from the sleep state to the non-sleep state. According to an embodiment of the disclosure, as the user's sleep state and a state immediately after the sleep state switches to the non-sleep state may be regarded as the relatively most stable state (e.g., a state in which the heartrate of the user is lowest), the exercise capacity may be largest when the user is in the sleep state and the state immediately after the sleep state switches to the non-sleep state. Therefore, according to an embodiment of the disclosure, the electronic device 100 may estimate the user's exercise capacity for the day based on the user's skin temperature and body temperature measured when the user is in the sleep state and/or the state immediately after the sleep state switches to the non-sleep state. According to an embodiment of the disclosure, the electronic device 100 may sense the user's skin temperature at any time before a predesignated time elapses after the user's state switches from the sleep state to the non-sleep state. According to another embodiment of the disclosure, the electronic device 100 may sense the user's skin temperature according to the user's selection input to a visual object set to sense the skin temperature, provided through the display module (e.g., the display module 860 of FIG. 8). According to still another embodiment of the disclosure, the electronic device 100 may sense the user's skin temperature according to the user's selection input to a physical key (e.g., a jog button or tactile key button) provided in the electronic device 100.

According to an embodiment of the disclosure, in operation 250, the electronic device 100 may determine the user's exercise capacity (e.g., a value defined as 0 to 100) using a "first temperature" and a "second temperature" determined based on the skin temperatures sensed in the sleep state and non-sleep state, respectively.

According to an embodiment of the disclosure, the electronic device 100 may estimate the user's body temperature based on the user's skin temperature sensed. According to an embodiment of the disclosure, the electronic device 100 may perform or control a function (or operation) of estimating a core body temperature as corrected based on the sensed skin temperature battery a designated correction value to calculate as the user's substantial body temperature. According to an embodiment of the disclosure, the core body temperature estimation by the electronic device 100 may include, e.g., correcting and/or compensating for the measured skin temperature with several pieces of ambient information or additional information. According to an embodiment of the disclosure, the electronic device 100 may estimate the user's body temperature using a lookup table that defines the relationship between the skin temperature and body temperature, stored in the electronic device 100. According to an embodiment of the disclosure, the electronic device 100 may estimate the body temperature from the user's skin temperature using an equation for estimating body temperature, stored in the electronic device 100. Other various techniques for estimating body temperature from the user's skin temperature may be applied to operation 250. According to an embodiment of the disclosure, the electronic device 100 may determine that a representative value (e.g., maximum value, minimum value, intermediate value, or average value) of the body temperatures sensed when the user is in the sleep state is a representative sleep body temperature (e.g., first temperature), and determine the user's exercise capacity based on the representative sleep body temperature and the temperature (e.g., second temperature) sensed immediately after switching to the non-sleep state. According to an embodiment of the disclosure, the electronic device 100 may determine the representative sleep body temperature among the body temperatures estimated based on the skin temperatures, respectively, sensed during sleep except for at least one of the lowest values and at least one of the highest values thereof. According to another embodiment of the disclosure, the electronic device 100 may determine that the lowest body temperature among the body temperatures estimated based on the skin temperatures, respectively, sensed during sleep is the first body temperature. According to an embodiment of the disclosure, the electronic device 100 may determine (e.g., calculate) the user's exercise capacity by substituting the estimated first body temperature and the estimated second body temperature into the first temperature and second temperature, respectively, which are variables of an equation. According to an embodiment of the disclosure, the coefficient of the equation above may be varied depending on the weight. For example, when a larger weight is set for the body temperature in the sleep state than the body temperature immediately after switching to the non-sleep state, the coefficient of the variable of the first temperature may be set to be larger than the coefficient of the variable of the second temperature. In contrast, when a smaller weight is set for the body temperature in the sleep state than the body temperature immediately after switching to the non-sleep state, the coefficient of the variable of the second temperature may be set to be larger than the coefficient of the variable of the first temperature. In this case, according to an embodiment of the disclosure, the equation may be determined previously (e.g., preset upon a manufacturing stage of the electronic device 100). According to an embodiment of the disclosure, the coefficient values included in the equation may repeatedly be changed according to the update of the operating system (OS) of the electronic device 100. According to an embodiment of the disclosure, the equation may be modeled with training data. According to an embodiment of the disclosure, the electronic device 100 may determine the coefficient (e.g., first coefficient) of the variable (e.g., first variable) of the first temperature and the coefficient (e.g., second coefficient) of the variable (e.g., second variable) of the second temperature using the training data provided from an external electronic device (e.g., the server 808 of FIG. 8). According to an embodiment of the disclosure, the training data may include a lookup table defining the relationship between the user's sleep time and the coefficient, determined empirically. According to an embodiment of the disclosure, the electronic device 100 may identify the user's sleep time and determine the first coefficient of the first variable by referring to the lookup table. To that end, according to an embodiment of the disclosure, the electronic device 100 may identify the user's sleep time.

According to another embodiment of the disclosure, the electronic device 100 may determine the user's exercise capacity based on the skin temperature. To that end, according to an embodiment of the disclosure, the electronic device 100 may determine that the representative value (e.g., maximum value, minimum value, intermediate value, or average value) of the "skin" temperatures sensed in the user's sleep state, instead of "body" temperature, as the variable of the equation, (hereinafter a "representative sleep skin temperature (e.g., first temperature)") The electronic device 100 according to an embodiment of the disclosure may substitute the representative sleep skin temperature as the variable value and determine the exercise capacity value. In this case, also, according to an embodiment of the disclosure, the electronic device 100 may determine the representative sleep skin temperature among the measured sleep skin temperatures sensed during sleep except for at least one of the lowest values and at least one of the highest values thereof. According to another embodiment of the disclosure, the electronic device 100 may determine that the lowest skin temperature among the skin temperatures sensed during sleep is the first temperature to be substituted in the equation according to an embodiment of the disclosure.

According to another embodiment of the disclosure, the electronic device 100 may determine the exercise capacity based on both skin temperature and body temperature. In this case, according to an embodiment of the disclosure, the equation may have both body temperature and skin temperature as variables, and the coefficient may be predetermined depending on the weights thereof. According to another embodiment of the disclosure, the user's exercise capacity may be determined based on a pre-stored lookup table. For example, according to an embodiment of the disclosure, the electronic device 100 may determine the exercise capacity using the lookup table defining the relationship between exercise capacity and certain information. The certain information may include information (e.g., change rate of body temperature during sleep) about a difference between the representative sleep body temperature (e.g., first reference body temperature) including the representative value during sleep during a predesignated period (e.g., one week) and the sleep body temperature (e.g., the first body temperature) estimated according to operation 250, and information (e.g., change rate of body temperature during non-sleep) about a difference between the representative non-sleep body temperature (e.g., second reference body temperature) including the representative value during non-sleep during the predesignated period (e.g., one week) and the body temperature (e.g., the second body temperature) estimated according to operation 250. For example, according to an embodiment of the disclosure, the lookup table may define that when the change rate of body temperature during sleep is +1.3%, and the change rate of body temperature immediately after wakeup is +1.6%, the exercise capacity may be determined to be reduced by 1.2%. According to another embodiment of the disclosure, the lookup table may define that when the change rate of representative sleep skin temperature (e.g., average sleep skin temperature) is +1.3%, and the change rate of skin temperature immediately after wakeup is +1.6%, the exercise capacity may be determined to be reduced by 1.2%.

According to an embodiment of the disclosure, the electronic device 100 may determine the change rate of the user's exercise capacity by referring to the lookup table. According to an embodiment of the disclosure, the exercise capacity may be changed by the user's physical features (e.g., height, weight, or body composition), the user's current state (e.g., condition), and/or the external environment (e.g., when the user is located in a high-illuminance area) exposed to the user. Accordingly, according to an embodiment of the disclosure, the electronic device 100 may calibrate the value, which indicates the exercise capacity determined according to the equation, based on the user's physical features (e.g., height, weight, or body composition), the user's current state (e.g., condition), and/or the external environment (e.g., whether the user is located in a high-illuminance area) exposed to the user. According to an embodiment of the disclosure, when the exercise capacity value determined based on the user's skin temperature and body temperature is "80," the electronic device 100 may calibrate the exercise capacity value "80" using the lookup table defining the relationship between the user's physical features and weights, pre-stored in the electronic device 100. For example, when the user is 185 cm tall, the electronic device 100 according to an embodiment of the disclosure may determine that the user's exercise capacity for the day is "88" by applying a weight (e.g., increasing 10%) stored in the lookup table. For example, according to an embodiment of the disclosure, when the user's current mood state is identified as "depressed," the electronic device 100 may determine that the user's exercise capacity for the day is "72" by applying a weight (e.g., decreasing 10%) stored in the lookup table. According to an embodiment of the disclosure, the electronic device 100 may receive information about the user's current mood state from the user. In another embodiment, the electronic device 100 may estimate the user's mood state using biometric information (e.g., pulse rate). For example, if the pulse rate is higher than the average pulse rate for the past week, the electronic device 100 may determine that the user's current state is an "excited" state and calibrate the exercise capacity value, accordingly.

According to an embodiment of the disclosure, in operation 260, the electronic device 100 may provide an exercise guide through a display (e.g., the display module 860 of FIG. 8) based on the exercise capacity determined according to operation 250. According to an embodiment of the disclosure, the electronic device 100 may provide an exercise guide based on the change rate of the determined exercise capacity value. For example, when the exercise capacity value determined according to operation 250 is, by exceeding a predesignated value (e.g., −1.0%), lower than the representative value (e.g., maximum value, minimum value, intermediate value, or average value) of the exercise capacity value during a predesignated period (e.g., one week), the electronic device 100 according to an embodiment of the disclosure may provide an exercise guide, such as "Exercise capacity today is lower than usual. Reduce exercise intensity and drink enough water," as an exercise guide (e.g., first exercise guide 340) as shown in FIG. 3C. According to an embodiment of the disclosure, as shown in FIG. 3D, the electronic device 100 may provide information about the change rate of body temperature and information about the change rate of exercise capacity along with the exercise guide (e.g., first exercise guide 340). According to an embodiment of the disclosure, when the exercise capacity value determined according to operation 250 falls between a predesignated range (e.g., +1.0% to −1.0%) with respect to the representative value (e.g., maximum value, minimum value, intermediate value, or average value) of the exercise capacity value during the predesignated period (e.g., one week), the electronic device 100 may provide an exercise guide, such as "Exercise capacity is the same level as usual. Do exercise at the same level as usual," as the exercise guide. According to an embodiment of the disclosure, when the exercise capacity value determined according to operation 250 is, by exceeding the predesignated value (e.g., +1.0%), higher than the representative value of the exercise capacity value during the predesignated period (e.g., one week), the electronic device 100 may provide an exercise guide, such as "Exercise capacity is higher than usual. You may do exercise at higher intensity than usual," as the exercise guide. According to an embodiment of the disclosure, as shown in FIG. 3A, the electronic device 100 may provide information (e.g., the change rate 310 of body temperature during sleep) about the difference between the representative sleep body temperature (e.g., maximum body temperature, minimum body temperature, intermediate body temperature, or average body temperature) during sleep during the predesignated period (e.g., one week) and the body temperature (e.g., first body temperature) estimated according to operation 250, information (e.g., the change rate 320 of body temperature during non-sleep) about the difference between the representative body temperature (e.g., maximum body temperature, minimum body temperature, intermediate body temperature, or average body temperature) during non-sleep during the predesignated period (e.g., one week) and the body temperature (e.g., second body temperature) estimated according to operation 250, and information (e.g., the change rate 330 of exercise capacity) about the difference between the representative value of the exercise capacity value during the predesignated period (e.g., one week) and the exercise capacity determined according to operation 250. According to another embodiment of the disclosure, as shown in FIG. 3B, the electronic device 100 may provide information (e.g., the change rate 310 of body temperature during sleep) about the difference between the representative sleep body temperature during sleep during the predesignated period (e.g., one week) and the body temperature (e.g., first body temperature) estimated according to operation 250, information (e.g., the change rate 312 of skin temperature during sleep) about the difference between the representative skin temperature during sleep during the predesignated period (e.g., one week) and the lowest skin temperature (or average skin temperature) among the skin temperatures sensed according to operation 250, information (e.g., the change rate 320 of body temperature during non-sleep) about the difference between the representative body temperature during non-sleep during the predesignated period (e.g., one week) and the body temperature (e.g., second body temperature) estimated according to operation 250, information (e.g., the change rate 322 of skin temperature during non-sleep) about the difference between the representative skin temperature during non-sleep during the predesignated period (e.g., one week) and the skin temperature sensed according to operation 250, and information (e.g., the change rate 330 of exercise capacity) about the difference between the representative exercise capacity value during the predesignated period (e.g., one week) and the exercise capacity value determined according to operation 250.

Figure 4:
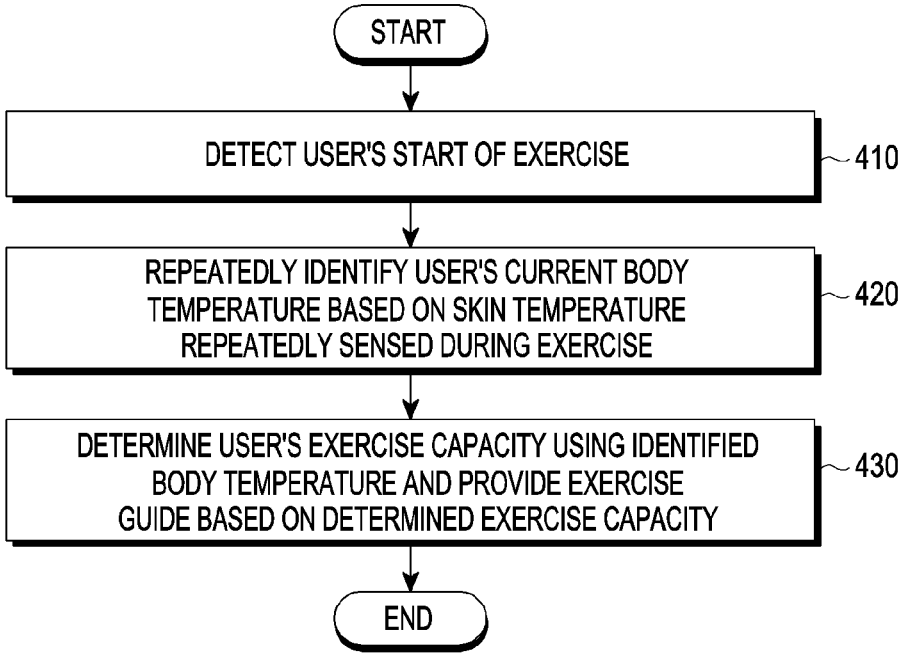
FIG. 4 is a flow chart illustrating a function or operation of determining a user's exercise capacity based on the user's body temperature sensed during the user's exercise and providing an exercise guide based on the determined exercise capacity, by an electronic device, according to an embodiment of the disclosure.
Figures 5A, 5B:
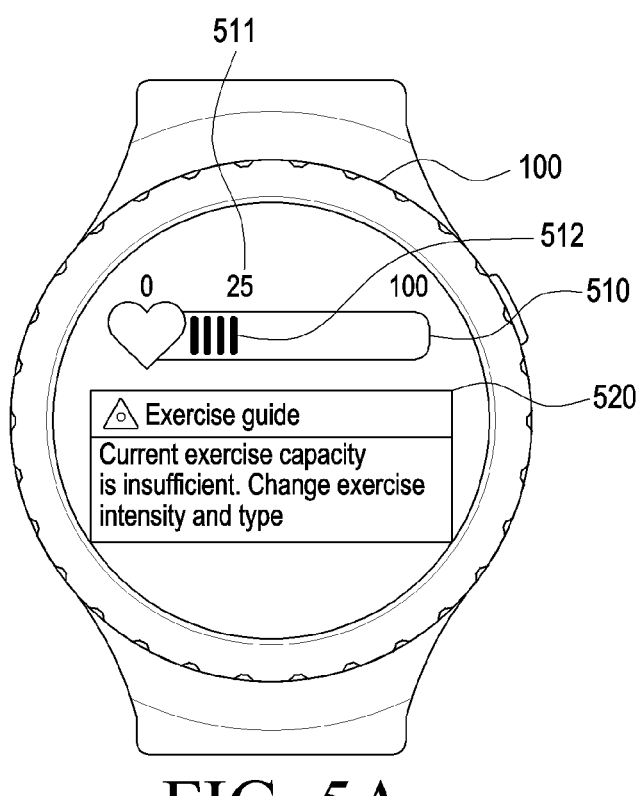
FIGS. 5A and 5B are example views illustrating a function or operation of providing information about a user's exercise capacity determined based on the user's body temperature sensed during the user's exercise and an exercise guide determined based on the exercise capacity, by an electronic device, according to an embodiment of the disclosure.

FIG. 4 is a flow chart illustrating a function or operation of determining a user's exercise capacity based on the user's skin temperature sensed during the user's exercise and providing an exercise guide based on the determined exercise capacity, by an electronic device, according to an embodiment of the disclosure. FIGS. 5A and 5B are example views illustrating a function or operation of providing information about a user's exercise capacity determined based on the user's skin temperature sensed during the user's exercise and an exercise guide determined based on the exercise capacity, by an electronic device, according to an embodiment of the disclosure.

Referring to FIG. 4, according to an embodiment of the disclosure, the electronic device 100 (e.g., the electronic device 801 of FIG. 8) may detect the user's start of exercise in operation 410. According to an embodiment of the disclosure, the electronic device 100 may determine that the user is in the exercise state when the magnitude (e.g., acceleration value) of the user's motion sensed by the sensor module 876 (e.g., the sensor module 876 of FIG. 8) (e.g., an accelerometer) is a preset value or more. According to an embodiment of the disclosure, the electronic device 100 may determine that the user is in the exercise state according to the user's selection input to a physical key or a specific visual object (e.g., a button indicating whether the exercise state is entered) provided through the electronic device 100. According to an embodiment of the disclosure, the electronic device 100 may determine that the user is in the exercise state if a time (e.g., 8:00 PM) preset by the user is reached. According to an embodiment of the disclosure, the electronic device 100 may determine whether the user is in the exercise state using data sensed by the sensor module 876 (e.g., a photoplethysmogram (PPG) sensor). For example, according to an embodiment of the disclosure, the electronic device 100 may determine that the user is in the exercise state when biometric information (e.g., blood pressure, heartrate, blood volume, pulse rate, or respiration rate) obtained based on sensing data (e.g., blood volume in blood vessel or change in blood volume in blood vessel) sensed by the sensor module 876 (e.g., a PPG sensor) is a predesignated value or more. Other various techniques for determining whether the user is in the exercise state may be applied to operation 410.

According to an embodiment of the disclosure, in operation 420, the electronic device 100 may repeatedly (e.g., every minute as the second period) identify (e.g., determine) the user's current body temperature based on the skin temperature sensed repeatedly (e.g., every 10 seconds as the first period) during exercise. According to an embodiment of the disclosure, the electronic device 100 may identify the user's body temperature based on the user's skin temperature obtained by the sensor module 876 (e.g., temperature sensor). According to an embodiment of the disclosure, the electronic device 100 may perform or control a function (or operation) of estimating a core body temperature corrected based on the sensed skin temperature and a designated correction value, to calculate it as the user's substantial body temperature. According to an embodiment of the disclosure, the core body temperature estimation by the electronic device 100 may include, e.g., correcting and/or compensating for the measured skin temperature with several pieces of ambient information or additional information. According to an embodiment of the disclosure, the electronic device 100 may determine the representative body temperature for a specific time (e.g., one minute) among the body temperatures repeatedly sensed during exercise except for at least one of the lowest body temperatures and at least one of the highest body temperatures thereof. According to an embodiment of the disclosure, the electronic device 100 may determine the user's current body temperature (e.g., representative body temperature during exercise) based on a determined representative skin temperature. According to an embodiment of the disclosure, the electronic device 100 may estimate the user's body temperature using a lookup table that defines the relationship between the skin temperature and body temperature, stored in the electronic device 100. According to an embodiment of the disclosure, the electronic device 100 may estimate the body temperature from the user's skin temperature using an equation for estimating body temperature, stored in the electronic device 100. Other various techniques for estimating body temperature from the user's skin temperature may be applied to operation 420. According to an embodiment of the disclosure, the electronic device 100 may obtain body temperature information sensed from an external electronic device (e.g., the electronic device 802 of FIG. 8) (e.g., a wireless earphone) and identify the user's current body temperature using the obtained body temperature information during exercise. According to another embodiment of the disclosure, the electronic device 100 may set body temperatures, estimated based on the skin temperatures, respectively, repeatedly (e.g., every minute as the first period) sensed "after" exercise, as representative body temperatures, respectively. In other words, according to an embodiment of the disclosure, the electronic device 100 may repeatedly (e.g., every minute as the second period) determine the user's exercise capacity using the body temperature estimated based on the skin temperature repeatedly (e.g., every minute as the first period) sensed.

According to an embodiment of the disclosure, in operation 430, the electronic device 100 may determine the user's exercise capacity using the body temperature (e.g., representative body temperature) determined according to operation 420 and provide an exercise guide based on the determined exercise capacity. According to an embodiment of the disclosure, the electronic device 100 may determine the user's exercise capacity using the lookup table defining the relationship between representative body temperature and exercise capacity value. According to an embodiment of the disclosure, when the exercise capacity value is included in a predesignated first range (e.g., 0 to 30 when 100 is the maximum), the electronic device 100 may provide an exercise guide, such as "Current exercise capacity is insufficient. Change the exercise intensity and type," as the exercise guide (e.g., the second exercise guide 520), along with the exercise capacity information 510, as shown in FIG. 5A. According to an embodiment of the disclosure, the exercise capacity information 510 may include an indicator 512 indicating the exercise capacity value and/or a number 511 indicating the exercise capacity value. According to another embodiment of the disclosure, the exercise capacity information 510 may be visually represented to correspond to the exercise capacity value. According to an embodiment of the disclosure, when the exercise capacity value is included in a predesignated first range (e.g., 0 to 30), the electronic device 100 may provide an exercise guide, such as "Current exercise capacity is insufficient. Take a rest or drink water," as the exercise guide (e.g., the third exercise guide 530), as shown in FIG. 5B. According to an embodiment of the disclosure, when the exercise capacity value is included in a predesignated second range (e.g., more than 30 and less than or equal to 70), the electronic device 100 may provide an exercise guide, such as "Current exercise intensity is appropriate." According to an embodiment of the disclosure, when the exercise capacity value is included in a predesignated third range (e.g., more than 70 and less than or equal to 100 when 100 is the maximum), the electronic device 100 may provide an exercise guide, such as "You may do exercise at higher intensity than the current exercise intensity." According to another embodiment of the disclosure, the electronic device 100 may determine one of the skin temperatures sensed according to the first period (e.g., 10 seconds) during the second period (e.g., one minute) as the representative skin temperature (e.g., the representative skin temperature during the second period during exercise) without estimating the user's body temperature and determine the user's exercise capacity based on the determined representative skin temperature. According to another embodiment of the disclosure, the electronic device 100 may determine that the skin temperature sensed according to the second period (e.g., one minute) is the representative temperature and determine the user's exercise capacity based on the determined representative skin temperature. According to another embodiment of the disclosure, the electronic device may determine the user's exercise capacity using both the representative skin temperature and the representative body temperature. In this case, according to an embodiment of the disclosure, the electronic device 100 may determine the user's exercise capacity by substituting the representative skin temperature and the representative body temperature in the equation according to an embodiment of the disclosure.

According to an embodiment, the operations 410 to 430 may be understood as performed by a processor (e.g., the processor 820 of FIG. 8) of an electronic device (e.g., the electronic device 801 of FIG. 8).

According to another embodiment, the operations 410 to 430 may be performed after the operation 260 of FIG. 2. In this case, the exercise capacity determined in the operation 430 may be referred as "re-determined" exercise capacity, and the skin temperature sensed in the operation 420 may be referred as "re-sensed" skin temperature.

Figure 6:
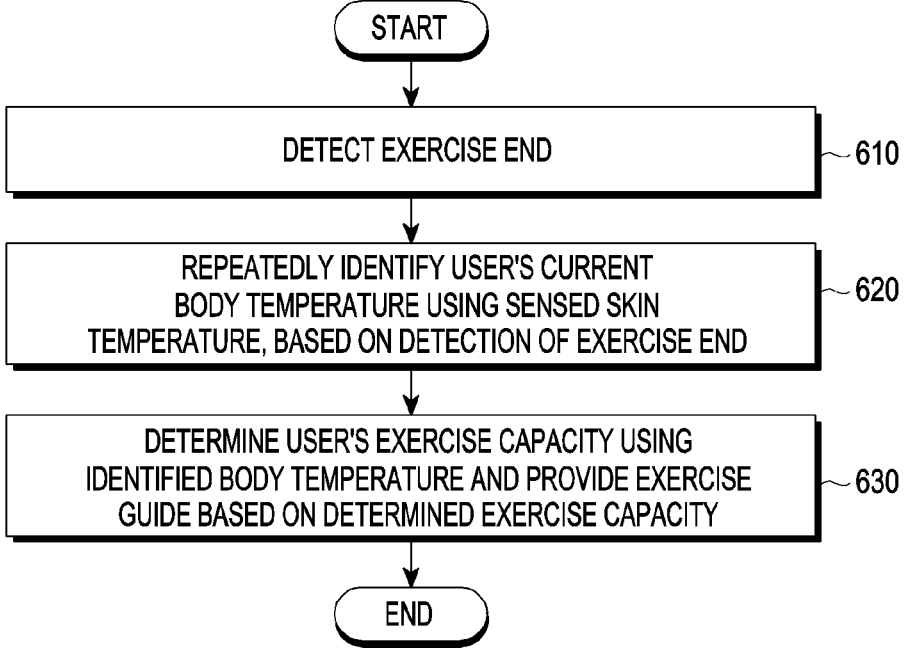
FIG. 6 is a flow chart illustrating a function or operation of determining a user's exercise capacity based on the user's body temperature sensed after the user's exercise and providing an exercise guide based on the determined exercise capacity, by an electronic device, according to an embodiment of the disclosure.
Figure 7A:
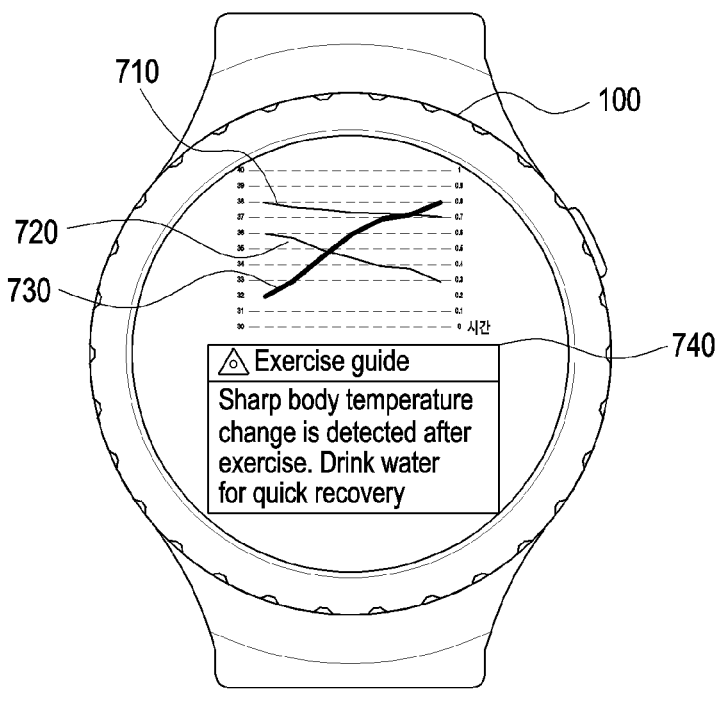
FIG. 7A is an example view illustrating a function or operation of providing information about a degree of change in a user's body temperature sensed after the user's exercise and an exercise guide determined based on the degree of change in the user's body temperature, by an electronic device, according to an embodiment of the disclosure.
Figure 7B:
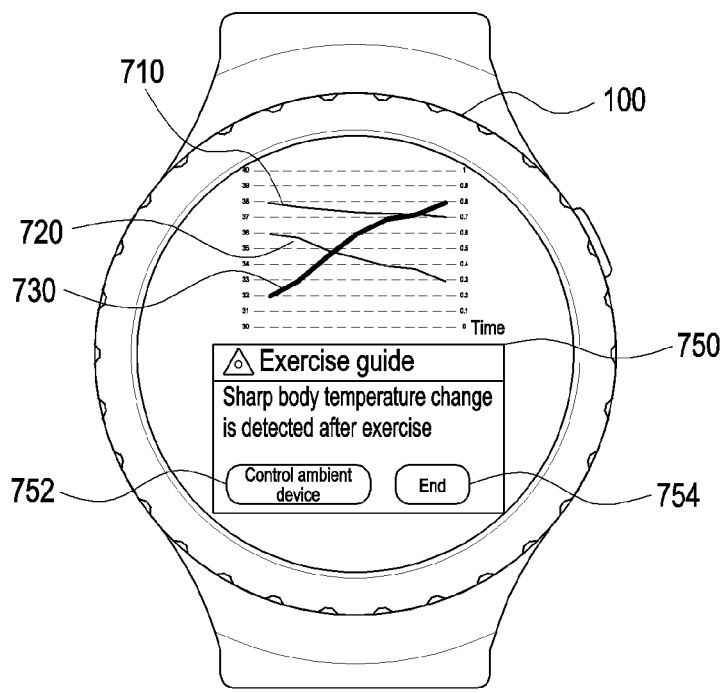
FIG. 7B is an example view illustrating a function or operation of providing a visual object for controlling an external electronic device based on a degree of change in a user's body temperature sensed after the user's exercise, by an electronic device according to an embodiment of the disclosure.

FIG. 6 is a flow chart illustrating a function or operation of determining a user's exercise capacity based on the user's body temperature sensed "after" the user's exercise and providing an exercise guide (e.g., fourth exercise guide 740 and/or fifth exercise guide 750) based on the determined exercise capacity, by an electronic device 100 (e.g., the electronic device 100 of FIGS. 1A to 1C or the electronic device 801 of FIG. 8), according to an embodiment of the disclosure. FIG. 7A is an example view illustrating a function or operation of providing information about a degree of change in a user's body temperature sensed after the user's exercise and an exercise guide determined based on the degree of change in the user's body temperature, by an electronic device 100, according to an embodiment of the disclosure. FIG. 7B is an example view illustrating a function or operation of providing a visual object for controlling an external electronic device based on a degree of change in a user's body temperature sensed after the user's exercise, by an electronic device 100 according to an embodiment of the disclosure.

Referring to FIG. 6, according to an embodiment of the disclosure, the electronic device 100 may detect an exercise end (i.e., exercise is ended) in operation 610. According to an embodiment of the disclosure, the electronic device 100 may determine that the user is in the exercise end state when the magnitude (e.g., acceleration value) of the user's motion sensed by the sensor module 876 (e.g., the sensor module 876 of FIG. 8) (e.g., an accelerometer) reduced to a preset value or less and keep the value for a preset period. According to an embodiment of the disclosure, the electronic device 100 may determine that the user is in the exercise end state according to the user's selection input to a physical key or a specific visual object (e.g., a button indicating whether the exercise end state is entered) provided through the electronic device 100. According to an embodiment of the disclosure, the electronic device 100 may determine that the user is in the exercise end state if a time (e.g., 9:00 PM) preset by the user is reached after the start of exercise is detected. According to an embodiment of the disclosure, the electronic device 100 may determine whether the user is in the exercise end state using data sensed by the sensor module 876 (e.g., a photoplethysmogram (PPG) sensor). For example, according to an embodiment of the disclosure, the electronic device 100 may determine that the user is in the exercise end state when biometric information (e.g., blood pressure, heartrate, blood volume, pulse rate, or respiration rate) obtained based on sensing data (e.g., blood volume in blood vessel or change in blood volume in blood vessel) sensed by the sensor module 876 (e.g., a PPG sensor) is a predesignated value or less. Other various techniques for determining whether the user is in the exercise state may be applied to operation 610.

According to an embodiment of the disclosure, in operation 620, the electronic device 100 may repeatedly (e.g., every minute) identify (e.g., determine) the user's current body temperature using the sensed skin temperature, based on detecting the exercise end. For example, according to an embodiment of the disclosure, the electronic device 100 may repeatedly (e.g., every minute as the second period) identify (e.g., determine) the user's current body temperature based on the skin temperature sensed repeatedly (e.g., every 10 seconds as the first period) after exercise ends. According to an embodiment of the disclosure, the electronic device 100 may identify the user's body temperature based on the user's skin temperature obtained by the sensor module 876 (e.g., temperature sensor). According to an embodiment of the disclosure, the electronic device 100 may determine the representative body temperature among the body temperatures estimated based on the skin temperatures, respectively, repeatedly (e.g., every 10 seconds as the first period) sensed during exercise except for at least one of the lowest body temperatures and at least one of the highest body temperatures thereof. According to an embodiment of the disclosure, the electronic device 100 may determine the user's current body temperature (e.g., representative body temperature in the exercise end state) based on a determined average skin temperature. According to an embodiment of the disclosure, the electronic device 100 may estimate the user's body temperature using a lookup table that defines the relationship between the skin temperature and body temperature, stored in the electronic device 100. According to an embodiment of the disclosure, the electronic device 100 may estimate the body temperature from the user's skin temperature using an equation for estimating body temperature, stored in the electronic device 100. Other various techniques for estimating body temperature from the user's skin temperature may be applied to operation 620. According to an embodiment of the disclosure, the electronic device 100 may obtain body temperature information sensed from an external electronic device (e.g., the electronic device 802 of FIG. 8) (e.g., a wireless earphone) and identify the user's current body temperature using the obtained body temperature information in the exercise end state. According to an embodiment of the disclosure, the electronic device 100 may set body temperatures, estimated based on the skin temperatures, respectively, repeatedly (e.g., every minute as the first period) sensed after exercise, as representative body temperatures, respectively. In other words, according to an embodiment of the disclosure, the electronic device 100 may repeatedly (e.g., every minute as the second period) determine the user's exercise capacity using the body temperature estimated based on the skin temperature repeatedly (e.g., every minute as the first period) sensed.

According to an embodiment of the disclosure, in operation 630, the electronic device 100 may determine the user's exercise capacity using the body temperature (e.g., representative body temperature) identified according to operation 620 and provide an exercise guide based on the determined exercise capacity. According to an embodiment of the disclosure, the electronic device 100 may determine the user's exercise capacity using the lookup table defining the relationship between representative body temperature and exercise capacity value. According to an embodiment of the disclosure, when the change rate per predesignated time (e.g., change rate per minute) of the exercise capacity value is included in a predesignated fourth range (e.g., more than 70% and less than or equal to 100%), the electronic device 100 may provide an exercise guide, such as "Sharp body temperature change is detected after exercise. Drink water for quick recovery," as the exercise guide (e.g., fourth exercise guide 740), along with the information 710 (e.g., change trend over time) about the skin temperature, the information 720 (e.g., change trend over time) about the body temperature, and the information 730 (e.g., change trend over time) about the exercise capacity, as shown in FIG. 7A. According to an embodiment of the disclosure, the information 710 (e.g., change trend over time) about the skin temperature, the information 720 (e.g., change trend over time) about the body temperature, and the information 730 (e.g., change trend over time) about the exercise capacity may be provided in the form of graphs as shown in FIGS. 7A and 7B so that the user may identify a change trend of the skin temperature, the body temperature, or the exercise capacity over time. According to an embodiment of the disclosure, when the change rate of the exercise capacity value is included in the predesignated fourth range (e.g., more than 70% and less than or equal to 100%), the electronic device 100 may provide an exercise guide, such as "Sharp body temperature change is detected after exercise," as the exercise guide (e.g., the fifth exercise guide 750), as shown in FIG. 7B. According to an embodiment of the disclosure, the electronic device 100 may determine an exercise guide using the lookup table defining the relationship between change rate per predesignated time (e.g., change rate per minute) of exercise capacity value and exercise guide. According to an embodiment of the disclosure, the exercise guide (e.g., the fifth exercise guide 750) may include a first menu 752 for controlling an ambient device (e.g., an internet of things (IOT) device) (e.g., control the temperature of the ambient device) and a second menu 754 for terminating the output of the exercise guide (e.g., the fifth exercise guide 750), as shown in FIG. 7B. According to an embodiment of the disclosure, if selection of the first menu 752 is identified, the electronic device 100 may execute an application for controlling the ambient device. According to an embodiment of the disclosure, the electronic device 100 may obtain a user input for controlling the ambient device through the executed application. According to an embodiment of the disclosure, the electronic device 100 may be directly connected with the ambient device (e.g., air conditioner or hot air fan) or connected to be operated with a hub device for controlling the ambient device (e.g., air conditioner or hot air fan). According to an embodiment of the disclosure, when the change rate per predesignated time (e.g., change rate per minute) of the exercise capacity value is included in a predesignated fifth range (e.g., 0% to 70%), the electronic device 100 may provide an exercise guide, such as "Current ambient temperature is appropriate. It is ok to keep the current temperature to maintain the exercise recovery state." According to an embodiment of the disclosure, the electronic device 100 may determine one of the skin temperatures sensed according to the first period (e.g., 10 seconds) during the second period (e.g., one minute) as the representative skin temperature (e.g., the average skin temperature during the second period in the exercise end state without estimating the user's body temperature and determine the user's exercise capacity based on the determined representative skin temperature. According to an embodiment of the disclosure, the electronic device 100 may determine that the skin temperature sensed according to the second period (e.g., one minute) is the representative temperature and determine the user's exercise capacity based on the determined representative skin temperature. According to another embodiment of the disclosure, the electronic device 100 may determine the user's exercise capacity using both the representative skin temperature and the representative body temperature. In this case, according to an embodiment of the disclosure, the electronic device 100 may determine the user's exercise capacity by substituting the representative skin temperature and the representative body temperature in the equation according to an embodiment of the disclosure.

Various embodiments of the disclosure may be performed through an external electronic device (e.g., the electronic device 802 of FIG. 8 or the electronic device 804 of FIG. 8) (e.g., a smartphone) connected to be operated with the electronic device 100. For example, according to an embodiment of the disclosure, the function or operation of estimating body temperature may be estimated by an external electronic device (e.g., a smartphone) based on information about the skin temperature transmitted from the electronic device 100 to the external electronic device (e.g., a smartphone). Further, according to an embodiment of the disclosure, the function or operation of determining exercise capacity may be performed by the external electronic device (e.g., a smartphone) based on various pieces of information provided from the electronic device 100.

According to an embodiment, operations 610 to 630 may be understood as performed by a processor (e.g., the processor 820 of FIG. 8) of an electronic device (e.g., the electronic device 801 of FIG. 8).

According to an embodiment of the disclosure, the function or operation of determining exercise capacity may be performed by a server (e.g., the server 808 of FIG. 8) based on various pieces of information provided from the electronic device 100. For example, according to an embodiment of the disclosure, the electronic device 100 may transmit information about a first body temperature (e.g., body temperature sensed in the user's sleep state) and a second body temperature (e.g., body temperature sensed in the user's non-sleep state) to the server, and the server may determine the user's exercise capacity. According to an embodiment of the disclosure, the server may transmit information about the determined user exercise capacity to the electronic device 100, and the electronic device 100 may provide information about the user's exercise capacity using the received exercise capacity information.

According to an embodiment of the disclosure, an electronic device 100 may include a sensor module (e.g., the sensor module 876 of FIG. 8), a display (e.g., the display module 860 of FIG. 8), and at least one processor (e.g., the processor 820 of FIG. 8) configured to determine whether a user of the electronic device is in a sleep state using the sensor module, repeatedly sense the user's skin temperature using the sensor module, based on determining that the user is in the sleep state, determine whether the user is in a non-sleep state using the sensor module while repeatedly sensing the user's skin temperature, sense the user's skin temperature using the sensor module, based on determining that the user is in the non-sleep state, determine the user's exercise capacity using the user's first temperature and second temperature determined based on the skin temperature sensed in the sleep state and the skin temperature sensed in the non-sleep state, respectively, and provide an exercise guide (e.g., the first exercise guide 340) through the display, based on the determined exercise capacity.

According to an embodiment of the disclosure, a method for controlling an electronic device 100 may include determining whether a user is in a sleep state using a sensor module (e.g., the sensor module 876 of FIG. 8) of the electronic device 100, repeatedly sensing the user's skin temperature using the sensor module, based on determining that the user is in the sleep state, determining whether the user is in a non-sleep state using the sensor module (e.g., the sensor module 876 of FIG. 8) while repeatedly sensing the user's skin temperature, sensing the user's skin temperature using the sensor module (e.g., the sensor module 876 of FIG. 8), based on determining that the user is in the non-sleep state, determining the user's exercise capacity using the user's first temperature and second temperature determined based on the skin temperature sensed in the sleep state and the skin temperature sensed in the non-sleep state, and providing an exercise guide (e.g., the first exercise guide 340) through a display (e.g., the display module 860 of FIG. 8) of the electronic device, based on the determined exercise capacity.

According to an embodiment of the disclosure, a method for controlling an electronic device 100 may include determining whether a user is doing exercise based on data sensed by a sensor module (e.g., the sensor module 876 of FIG. 8) of an electronic device 100, repeatedly sensing the user's skin temperature using the sensor module during the exercise, repeatedly identifying the user's current body temperature based on the sensed skin temperature, determining the user's exercise capacity using the identified body temperature, and providing an exercise guide (e.g., the first exercise guide 520) through a display (e.g., the display module 860 of FIG. 8) of the electronic device, based on the determined exercise capacity.

FIG. 8 is a block diagram illustrating an electronic device 801 in a network environment 800 according to various embodiments. Referring to FIG. 8, the electronic device 801 in the network environment 800 may communicate with at least one of an electronic device 802 via a first network 898 (e.g., a short-range wireless communication network), or an electronic device 804 or a server 801 via a second network 899 (e.g., a long-range wireless communication network). According to an embodiment, the electronic device 801 may communicate with the electronic device 804 via the server 801. According to an embodiment, the electronic device 801 may include a processor 820, memory 830, an input module 850, a sound output module 855, a display module 860, an audio module 870, a sensor module 876, an interface 877, a connecting terminal 878, a haptic module 879, a camera module 880, a power management module 888, a battery 889, a communication module 890, a subscriber identification module (SIM) 896, or an antenna module 897. In some embodiments, at least one (e.g., the connecting terminal 878) of the components may be omitted from the electronic device 801, or one or more other components may be added in the electronic device 101. According to an embodiment, some (e.g., the sensor module 876, the camera module 880, or the antenna module 897) of the components may be integrated into a single component (e.g., the display module 860).

The processor 820 may execute, for example, software (e.g., a program 840) to control at least one other component (e.g., a hardware or software component) of the electronic device 801 coupled with the processor 820, and may perform various data processing or computation. According to one embodiment, as at least part of the data processing or computation, the processor 820 may store a command or data received from another component (e.g., the sensor module 876 or the communication module 890) in volatile memory 832, process the command or the data stored in the volatile memory 832, and store resulting data in non-volatile memory 834. According to an embodiment, the processor 820 may include a main processor 821 (e.g., a central processing unit (CPU) or an application processor (AP)), or an auxiliary processor 823 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 801 includes the main processor 821 and the auxiliary processor 823, the auxiliary processor 823 may be configured to use lower power than the main processor 821 or to be specified for a designated function. The auxiliary processor 823 may be implemented as separate from, or as part of the main processor 821.

The auxiliary processor 823 may control at least some of functions or states related to at least one component (e.g., the display module 860, the sensor module 876, or the communication module 890) among the components of the electronic device 801, instead of the main processor 821 while the main processor 821 is in an inactive (e.g., sleep) state, or together with the main processor 821 while the main processor 821 is in an active state (e.g., executing an application). According to an embodiment, the auxiliary processor 823 (e.g., an image signal processor or a communication processor) may be implemented as part of another component (e.g., the camera module 880 or the communication module 890) functionally related to the auxiliary processor 123. According to an embodiment, the auxiliary processor 823 (e.g., the neural processing unit) may include a hardware structure specified for artificial intelligence model processing. The artificial intelligence model may be generated via machine learning. Such learning may be performed, e.g., by the electronic device 801 where the artificial intelligence is performed or via a separate server (e.g., the server 801). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 830 may store various data used by at least one component (e.g., the processor 820 or the sensor module 876) of the electronic device 801. The various data may include, for example, software (e.g., the program 840) and input data or output data for a command related thereto. The memory 830 may include the volatile memory 832 or the non-volatile memory 834.

The program 840 may be stored in the memory 830 as software, and may include, for example, an operating system (OS) 842, middleware 844, or an application 846.

The input module 850 may receive a command or data to be used by other component (e.g., the processor 820) of the electronic device 801, from the outside (e.g., a user) of the electronic device 801. The input module 850 may include, for example, a microphone, a mouse, a keyboard, keys (e.g., buttons), or a digital pen (e.g., a stylus pen).

The sound output module 855 may output sound signals to the outside of the electronic device 801. The sound output module 855 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 860 may visually provide information to the outside (e.g., a user) of the electronic device 801. The display 860 may include, for example, a display, a hologram device, or a projector and control circuitry to control a corresponding one of the display, hologram device, and projector. According to an embodiment, the display 860 may include a touch sensor configured to detect a touch, or a pressure sensor configured to measure the intensity of a force generated by the touch.

The audio module 870 may convert a sound into an electrical signal and vice versa. According to an embodiment, the audio module 870 may obtain the sound via the input module 850, or output the sound via the sound output module 855 or a headphone of an external electronic device (e.g., an electronic device 802) directly (e.g., wiredly) or wirelessly coupled with the electronic device 801.

The sensor module 876 may detect an operational state (e.g., power or temperature) of the electronic device 801 or an environmental state (e.g., a state of a user) external to the electronic device 101, and then generate an electrical signal or data value corresponding to the detected state. According to an embodiment, the sensor module 876 may include, for example, a gesture sensor, a gyro sensor, an atmospheric pressure sensor, a magnetic sensor, an accelerometer, a grip sensor, a proximity sensor, a color sensor, an infrared (IR) sensor, a biometric sensor, a temperature sensor, a humidity sensor, or an illuminance sensor.

The interface 877 may support one or more specified protocols to be used for the electronic device 801 to be coupled with the external electronic device (e.g., the electronic device 802) directly (e.g., wiredly) or wirelessly. According to an embodiment, the interface 877 may include, for example, a high definition multimedia interface (HDMI), a universal serial bus (USB) interface, a secure digital (SD) card interface, or an audio interface.

A connecting terminal 878 may include a connector via which the electronic device 801 may be physically connected with the external electronic device (e.g., the electronic device 802). According to an embodiment, the connecting terminal 878 may include, for example, a HDMI connector, a USB connector, a SD card connector, or an audio connector (e.g., a headphone connector).

The haptic module 879 may convert an electrical signal into a mechanical stimulus (e.g., a vibration or motion) or electrical stimulus which may be recognized by a user via his tactile sensation or kinesthetic sensation. According to an embodiment, the haptic module 879 may include, for example, a motor, a piezoelectric element, or an electric stimulator.

The camera module 880 may capture a still image or moving images. According to an embodiment, the camera module 880 may include one or more lenses, image sensors, image signal processors, or flashes.

The power management module 888 may manage power supplied to the electronic device 801. According to one embodiment, the power management module 888 may be implemented as at least part of, for example, a power management integrated circuit (PMIC).

The battery 889 may supply power to at least one component of the electronic device 801. According to an embodiment, the battery 889 may include, for example, a primary cell which is not rechargeable, a secondary cell which is rechargeable, or a fuel cell.

The communication module 890 may support establishing a direct (e.g., wired) communication channel or a wireless communication channel between the electronic device 801 and the external electronic device (e.g., the electronic device 802, the electronic device 804, or the server 801) and performing communication via the established communication channel. The communication module 890 may include one or more communication processors that are operable independently from the processor 820 (e.g., the application processor (AP)) and supports a direct (e.g., wired) communication or a wireless communication. According to an embodiment, the communication module 890 may include a wireless communication module 892 (e.g., a cellular communication module, a short-range wireless communication module, or a global navigation satellite system (GNSS) communication module) or a wired communication module 894 (e.g., a local area network (LAN) communication module or a power line communication (PLC) module). A corresponding one of these communication modules may communicate with the external electronic device 804 via a first network 898 (e.g., a short-range communication network, such as Bluetooth™, wireless-fidelity (Wi-Fi) direct, or infrared data association (IrDA)) or a second network 899 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 892 may identify or authenticate the electronic device 801 in a communication network, such as the first network 898 or the second network 899, using subscriber information (e.g., international mobile subscriber identity (IMSI)) stored in the subscriber identification module 896.

The wireless communication module 892 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 892 may support a high-frequency band (e.g., the mmWave band) to achieve, e.g., a high data transmission rate. The wireless communication module 892 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 892 may support various requirements specified in the electronic device 801, an external electronic device (e.g., the electronic device 804), or a network system (e.g., the second network 899). According to an embodiment, the wireless communication module 892 may support a peak data rate (e.g., 20 Gbps or more) for implementing eMBB, loss coverage (e.g., 864 dB or less) for implementing mMTC, or U-plane latency (e.g., 0.5 ms or less for each of downlink (DL) and uplink (UL), or a round trip of 8 ms or less) for implementing URLLC.

The antenna module 897 may transmit or receive a signal or power to or from the outside (e.g., the external electronic device). According to an embodiment, the antenna module 897 may include one antenna including a radiator formed of a conductor or conductive pattern formed on a substrate (e.g., a printed circuit board (PCB)). According to an embodiment, the antenna module 897 may include a plurality of antennas (e.g., an antenna array). In this case, at least one antenna appropriate for a communication scheme used in a communication network, such as the first network 898 or the second network 899, may be selected from the plurality of antennas by, e.g., the communication module 890. The signal or the power may then be transmitted or received between the communication module 890 and the external electronic device via the selected at least one antenna. According to an embodiment, other parts (e.g., radio frequency integrated circuit (RFIC)) than the radiator may be further formed as part of the antenna module 897.

According to various embodiments, the antenna module 897 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 801 and the external electronic device 804 via the server 801 coupled with the second network 899. The external electronic devices 802 or 804 each may be a device of the same or a different type from the electronic device 801. According to an embodiment, all or some of operations to be executed at the electronic device 801 may be executed at one or more of the external electronic devices 802, 804, or 801. For example, if the electronic device 801 should perform a function or a service automatically, or in response to a request from a user or another device, the electronic device 801, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 801. The electronic device 801 may provide the outcome, with or without further processing of the outcome, as at least part of a reply to the request. To that end, a cloud computing, distributed computing, mobile edge computing (MEC), or client-server computing technology may be used, for example. The electronic device 801 may provide ultra low-latency services using, e.g., distributed computing or mobile edge computing. In another embodiment, the external electronic device 804 may include an Internet-of-things (IOT) device. The server 801 may be an intelligent server using machine learning and/or a neural network. According to an embodiment, the external electronic device 804 or the server 801 may be included in the second network 899. The electronic device 801 may be applied to intelligent services (e.g., smart home, smart city, smart car, or healthcare) based on 5G communication technology or IoT-related technology.

The electronic device according to various embodiments of the disclosure may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 820) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to an embodiment of the disclosure, each component (e.g., a module or a program) of the above-described components may include a single entity or multiple entities. Some of the plurality of entities may be separately disposed in different components. According to an embodiment of the disclosure, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to an embodiment of the disclosure, operations performed by the module, the program, or another component may be carried out sequentially, in parallel, repeatedly, or heuristically, or one or more of the operations may be executed in a different order or omitted, or one or more other operations may be added.

What is claimed is:
1. An electronic device comprising:
memory storing instructions;
a sensor module;
a display; and
at least one processor, wherein the instructions cause the electronic device to:
determine whether a user of the electronic device is in a sleep state using the sensor module,
repeatedly detect a skin temperature of the user using the sensor module, based on determining that the user is in the sleep state,
determine whether the user is in a non-sleep state using the sensor module while repeatedly detecting the skin temperature of the user,

detect the skin temperature of the user using the sensor module, based on determining that the user is in the non-sleep state,
determine an exercise capacity of the user using a first body temperature of the user and a second body temperature of the user determined based on the skin temperature detected in the sleep state and the skin temperature detected in the non-sleep state, respectively, wherein the exercise capacity is determined by comparing a first reference body temperature stored in the memory with the first body temperature in the sleep state and comparing a second reference body temperature stored in the memory with the second body temperature in the non-sleep state, and
based on the determined exercise capacity, provide, through the display, an exercise guide including a recommendation message for an exercise strength corresponding to the exercise capacity.
2. The electronic device of claim 1, wherein the instructions further cause the electronic device to provide a change rate of the exercise capacity through the display.
3. The electronic device of claim 1, wherein the non-sleep state includes a state within a predesignated time after the user switches from the sleep state to the non-sleep state.
4. The electronic device of claim 1, wherein the instructions further cause the electronic device to determine the exercise capacity further based on the user's ambient environment or the user's body feature.
5. A method for controlling an electronic device, the method comprising:
determining whether a user is in a sleep state using a sensor module of the electronic device,
repeatedly sensing a skin temperature of the user using the sensor module, based on determining that the user is in the sleep state,
determining whether the user is in a non-sleep state using the sensor module while repeatedly sensing the skin temperature of the user,
sensing the skin temperature of the user using the sensor module, based on determining that the user is in the non-sleep state,
determining an exercise capacity of the user using a first body temperature of the user and a second body temperature of the user determined based on the skin temperature sensed in the sleep state and the skin temperature sensed in the non-sleep state, respectively, wherein the exercise capacity is determined by comparing a first reference body temperature stored in the memory with the first body temperature in the sleep state and comparing a second reference body temperature stored in the memory with the second body temperature in the non-sleep state, and
based on the determined exercise capacity, providing, through a display of the electronic device, an exercise guide including a recommendation message for an exercise strength corresponding to the exercise capacity.
6. The method of claim 5, further comprising providing a change rate of the exercise capacity through the display.
7. The method of claim 5, wherein the non-sleep state includes a state within a predesignated time after the user switches from the sleep state to the non-sleep state.
8. The method of claim 5, wherein the determining of the exercise capacity is performed further based on the user's ambient environment or the user's body feature.

9. The method of claim 5, further comprising:

determining whether the user is doing exercise based on data sensed by the sensor module, and upon determining that the user is doing exercise, re-determining the exercise capacity.

10. The method of claim 9, further comprising:

providing, through the display, information about the re-determined exercise capacity along with the exercise guide.

11. The method of claim 5, further comprising:

determining whether the user ends the exercise based on data sensed by the sensor module, and upon determining that the user ends the exercise, re-sensing the user's skin temperature using the sensor module within a predesignated time from a time when the exercise ends.

12. The method of claim 11, further comprising:

re-determining the exercise capacity based on the re-sensed skin temperature.

13. The method of claim 12, further comprising:

providing, through the display, a change trend for the re-determined exercise capacity and a change trend of the skin temperature from the time when the exercise ends.

* * * * *